United States Patent [19]

Winter et al.

[11] Patent Number: 5,545,782

[45] Date of Patent: Aug. 13, 1996

[54] METHOD FOR INHIBITING PREMATURE POLYMERIZATION OF VINYL AROMATIC MONOMERS

[75] Inventors: Roland A. E. Winter, Armonk; Volker H. von Ahn, Mahopac, both of N.Y.

[73] Assignee: Ciba-Geigy Corporation, Tarrytown, N.Y.

[21] Appl. No.: 443,051

[22] Filed: May 17, 1995

Related U.S. Application Data

[60] Division of Ser. No. 383,279, Feb. 3, 1995, which is a continuation-in-part of Ser. No. 345,097, Nov. 28, 1994, abandoned.

[51] Int. Cl.⁶ ..................................................... C07C 7/20
[52] U.S. Cl. ................... 585/5; 585/4; 585/435; 585/832
[58] Field of Search ............................ 385/3, 4, 5, 832, 385/422, 435

[56] References Cited

U.S. PATENT DOCUMENTS

| | | |
|---|---|---|
| 3,733,326 | 5/1973 | Murayama et al. . |
| 3,988,212 | 10/1976 | Watson ........................................ 203/9 |
| 4,466,904 | 8/1984 | Watson et al. ........................... 252/402 |
| 4,468,343 | 8/1984 | Butler et al. ............................. 252/403 |
| 5,254,760 | 10/1993 | Winter et al. . |

FOREIGN PATENT DOCUMENTS

| | | |
|---|---|---|
| 0581737 | 2/1994 | European Pat. Off. . |
| 1165534 | 6/1989 | Japan . |
| 1027150 | 7/1983 | U.S.S.R. . |
| 1139722 | 2/1985 | U.S.S.R. . |
| 1558888 | 4/1990 | U.S.S.R. . |
| 1218456 | 1/1971 | United Kingdom . |
| 9503263 | 2/1995 | WIPO . |

OTHER PUBLICATIONS

Polymers Bulletin 6, 589–593 (1982).
Die Makro Molekulare Chemie 160 (1972) 243–249.
Derwent 91–085387/12.
Derwent 85–222317/36.
Derwent 84–094116/15.
Angew Chem. 67 (1955) No. 2 45–52.
Vysokamal. Sayed A17:No. 8, 1671–1677 (1975).

*Primary Examiner*—Asok Pal
*Assistant Examiner*—Bekir L. Yildirim
*Attorney, Agent, or Firm*—Luther A. R. Hall

[57] ABSTRACT

Nitroxyl inhibitors in combination with some oxygen reduce the premature polymerization of vinyl aromatic monomers during the manufacturing processes for such monomers. Even small quantities of air used in combination with the nitroxyl inhibitors result in vastly prolonged inhibition times for said monomers.

11 Claims, No Drawings

METHOD FOR INHIBITING PREMATURE POLYMERIZATION OF VINYL AROMATIC MONOMERS

This is a divisional of application Ser. No. 08/383,279, filed on Feb. 3,1995, which is a continuation-in-part of application Ser. No. 08/345,097, filed on Nov. 28, 1994, now abandoned.

This invention pertains to the compositions, processes and methods of using nitroxyl inhibitors, particularly in combination with oxygen, to prevent the premature polymerization of vinyl aromatic monomers.

BACKGROUND OF THE INVENTION

It is well known that vinyl aromatic monomer compounds such as styrene or α-methylstyrene, have a strong tendency to polymerize when subjected to elevated temperatures. Manufacturing processes for such monomers typically include distillations at elevated temperatures.

To prevent premature polymerization of vinyl aromatic monomers during the distillation purification process, various compounds have been disclosed as polymerization inhibitors. These include elemental sulfur and many classes of organic chemicals. These materials have met with varying degrees of success in industrial use. Included among these organic materials are nitrated phenol derivatives, C- and N-nitroso compounds and nitroxyl derivatives. A particularly effective class of such inhibitors are hindered amine nitroxyls. This class of stable free radicals is characterized by having a NO* group, where the * asterisk denotes an unpaired electron, and where the nitrogen atom is further flanked by two carbon atoms, to neither of which hydrogen atoms are attached. Often these flanking carbon atoms are further connected by various bridging groups to form cyclic structures, such as, for example, six-membered piperidines, piperazines, five membered pyrollidines and the like. Collectively these stable free nitroxyl radicals (also called nitroxides) are referred to as "hindered amine" nitroxyl free radicals. Compounds of this class are not only valuable inhibitors of free radical-initiated polymerization in unsaturated monomers, but also have found uses as spin labels in biochemical applications.

Soviet Patent No. 1,027,150 discloses the stabilization of styrene by using nitroxyl radical. Soviet Patent No. 1,139, 722 discloses the use of a bis-nitroxyl radical as the thermal polymerization inhibitor for styrene. Japanese Hei 1-165534 discloses the use of 1-piperidyloxy derivatives as polymerization inhibitors for styrene. Soviet Patent No. 1,558,888 discloses the polymerization inhibition of styrene by a nitroxyl radical. U.S. Pat. No. 3,733,326 discloses the polymerization inhibition of vinyl monomers by free radical precursors. The inhibition of styrene polymerization by some hindered amine nitroxyl derivatives is also discussed by Y. Miura, S. Masuda, and M. Kinoshita, *Die Makromolekulare Chemie*, 1972, 160, 243–249, M. D. Gold'fein, E. A. Ragikov, V. N. Kozhevnikov, A. D. Stepukhovich and A. V. Trubnikov, *Vysokomol.soyed*, 1975, A17 (8), 1671–1677 translated in *Polymer Science (USSR)*, 1975, A17(8), 1919–1927 and by G. Moad, E. Rizzardo, and D. H. Solomon, *Polymer Bulletin* 1982, 6, 589–593. Inhibition of polymerization of vinyl aromatic compounds by a combination of a stable nitroxyl compound with aromatic nitro compounds is the subject of U.S. Pat. No. 5,254,760 (1993).

OBJECTS OF THE INVENTION

One object of the present invention is to provide a composition comprising a vinyl aromatic compound, and an effective amount of nitroxyl inhibitor and oxygen or air to optimize the effectiveness of the inhibitor.

Another object of the invention is to provide a process for the highly efficient utilization of nitroxyl inhibitors.

SUMMARY OF THE INVENTION

It is now been found that the effectiveness of nitroxyl inhibitors in vinyl aromatic monomers can be boosted substantially by the concomitant presence of small quantities of oxygen or air. The inhibition time, i.e the time to the onset of polymerization, is thus typically increased two- to four-fold, compared to completely oxygen free conditions. In some cases the continuous or intermittent addition of air throughout a distillation run may not be desirable where oxygen-free conditions are preferred as standard operating mode. In such cases, the insertion of air into the system can still be employed to quench instantly any polymerization that may have started during upset conditions, thus to avert any disastrous runaway polymerizations from occurring.

The method of boosting inhibiting activity with air or oxygen is particularly noteworthy and unobvious in view of existing literature indicating that oxygen does catalyze rather than inhibit thermal styrene polymerization (P. D. Bartlett, *Angew. Chem.*, 67, 45–52 (1955), even though oxygen is known to inhibit the polymerization of other monomers such as acrylic monomers.

DETAILED DISCLOSURE

The instant invention pertains to a composition which comprises (a) a vinyl aromatic compound, and (b) an effective inhibiting amount, sufficient to prevent premature polymerization during distillation or purification of said vinyl aromatic compound, of a stable hindered nitroxyl compound used together with an effective amount of oxygen or air to enhance the inhibiting activity of the nitroxyl compound.

The effective amount of nitroxyl compound is from 1 to 2000 ppm, based on the weight of component (a).

Preferably the amount of nitroxyl compound is from 5 to 1000 ppm, based on the weight of component (a).

The effective amount of oxygen or air is 10 ppm to about 1000 ppm, based on the weight of component (a). The upper practical limit for this amount will be determined by safety considerations.

The vinyl aromatic monomer of component (a) is selected from the group consisting of styrene, α-methylstyrene, vinyltoluene, divinylbenzene, styrenesulfonic acid and structural isomers, derivatives of said compounds and mixtures thereof.

Preferably, the vinyl aromatic monomer is styrene, α-methylstyrene, vinyltoluene or divinylbenzene; most preferably styrene.

The instant invention also pertains to a process for inhibiting the premature polymerization of a vinyl aromatic compound during distillation or purification which comprises incorporating therein an effective inhibiting amount, sufficient to prevent premature polymerization during distillation or purification of said vinyl aromatic compound, of a stable hindered nitroxyl compound used together with an effective amount of oxygen or air to enhance the inhibiting activity of the nitroxyl compound.

The vinyl aromatic compound is distilled or purified at a temperature from 50° C. to 150° C. The stable nitroxyl compound is added to the vinyl aromatic compound continuously or intermittently upstream to the point where distillation or purification occurs; or the stable nitroxyl compound can be added at different entry points into the vinyl aromatic compound process stream prior to the point where distillation or purification occurs.

The instant process can be started under either anaerobic or aerobic conditions with air or oxygen then being added continuously or intermittently thereafter to the vinyl aromatic monomer to prolong polymerization inhibition time or to short-stop incipient polymerization.

The term vinyl aromatic monomer includes any of readily polymerizable vinyl aromatic compounds, e.g. styrene, α-methylstyrene, vinyltoluene, divinylbenzene, styrenesulfonic acid and structural isomers, and derivatives and mixtures thereof. This invention is applicable to hindered amine nitroxyl radicals in general, i.e. compounds having at least one NO* group, where the * asterisk denotes an unpaired electron, and the nitrogen atom is further flanked by two carbon atoms, to neither of which hydrogen atoms are attached. These flanking carbon atoms may be further connected by various bridging groups to form cyclic structures such as for example six-membered piperidines, piperazines, five membered pyrollidines and the like, as exemplified by, but not limited to the list below:

di-tert-butyl nitroxyl, 1-oxyl-2,2,6,6-tetramethylpiperidine, 1-oxyl-2,2,6,6-tetramethylpiperidin-4-ol, 1-oxyl-2,2,6,6-tetramethylpiperidin-4-one, 1-oxyl-2,2,6,6-tetramethylpiperidin-4-yl acetate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl 4-tert-butylbenzoate, bis(1-oxyl-2,2,6,6-tetramethylpiperidin-4-yl)succinate, bis(1-oxyl-2,2,6,6-tetramethylpiperidin-4-yl)adipate, bis(1-oxyl-2,2,6,6-tetramethylpiperidin-4-yl)sebacate, bis(1-oxyl-2,2,6,6-tetramethylpiperidin-4-yl)n-butylmalonate, bis(1-oxyl-2,2,6,6-tetramethylpiperidin-4-yl)phthalate, bis(1-oxyl-2,2,6,6-tetramethylpiperidin-4-yl)isophthalate, bis(1-oxyl-2,2,6,6-tetramethylpiperidin-4-yl)terephthalate, bis(1-oxyl-2,2,6,6-tetramethylpiperidin-4-yl)hexahydroterephthalate, N,N'-bis(1-oxyl-2,2,6,6-tetramethylpiperidin-4-yl)adipamide, N-(1-oxyl-2,2,6,6-tetramethylpiperidin-4-yl)caprolactam, N-(1-oxyl-2,2,6,6-tetramethylpiperidin-4-yl)dodecylsuccinimide, 2,4,6-tris-(1-oxyl-2,2,6,6-tetramethylpiperidin-4-yl)cyanurate, 2,4,6-tris-[N-butyl-N-(1-oxyl-2,2,6,6-tetramethylpiperidin-4-yl]-s-triazine, or 4,4'-ethylenebis(1-oxyl-2,2,6,6-tetramethylpiperazin-3-one).

The effective amount of polymerization inhibitors added may vary over wide ranges depending upon the particular vinyl aromatic compound and the conditions of distillation. Preferably, the total amount of a nitroxyl radical is from 1 ppm to about 2,000 ppm based upon the weight of the monomer being inhibited. For most applications, the inhibitor system is used in the range of 5 to 1,000 ppm. As the temperature increases, greater amounts of inhibitor are required. During distillation of the vinyl aromatic mixtures, the temperature of the reboiler is in the range of 50° C. to about 150° C. The polymerization inhibitor can be introduced into the monomer to be protected by any conventional method. It may be added as a concentrate solution in suitable solvents just upstream of the point of desired application by any suitable means. Since the inhibitor is gradually depleted during operation, it is generally necessary to maintain the appropriate amount of the inhibitor in the distillation apparatus by adding inhibitor during the course of the distillation process. Such addition may be carried out either on a generally continuous basis or it may consist of intermittently charging inhibitor into the distillation system when the concentration of inhibitor is to be maintained above the minimum required level.

It is also within the purview of the instant invention that the vinyl aromatic monomer may also contain a solvent such as ethylbenzene or contain dissolved polymer such a saturated or unsaturated polyester.

The examples below illustrate the invention in a series of batch experiments. It is obvious to those skilled in the art that the invention is equally applicable to continuous processes and steady state conditions, typical of industrial manufacturing processes for vinyl aromatic monomers.

The following examples will serve to further illustrate the invention. In the examples, styrene, which is representative of vinyl aromatic monomers, is used as the test monomer.

EXAMPLES 1–5

Commercial grade styrene is freed of tert-butyl catechol storage stabilizer by washing with 1N sodium hydroxide solution, water and subsequent distillation under reduced pressure. A 300 mL 3-necked flask equipped with thermometer, condenser, rubber septum and magnetic stirrer bar is charged with 100 g of styrene, purified as described above, and 50 mg of bis(1-oxyl-2,2,6,6-tetramethylpiperidin-4-yl)sebacate, to give a 500 ppm solution of this representative nitroxyl inhibitor.

An oxygen-free atmosphere is established by five consecutive evacuations and backfilling with nitrogen, followed by sparging the styrene solution with pure nitrogen for 15 minutes. The vessel is immersed into a mechanically stirred and thermostatically controlled oil bath at 120° C. Samples are withdrawn at twenty minute intervals, and the amount of polystyrene formed is then determined by refractive index measurements which in turn are calibrated with authentic polystyrene in styrene solutions of known concentration. The onset of polymerization occurs abruptly at the end of a characteristic induction period. The length of this induction period the "inhibition time" is determined experimentally by extrapolating the linear polymer/time curve.

Under anaerobic condition the inhibition time is 50 minutes. Under a static air atmosphere the inhibition time almost tripled to 147 minutes. It is further demonstrated that even minute quantities of air bring about vastly enhanced inhibition times. Thus, air is sparged continuously at 0.4 mL/min into a previously rigorously anaerobic system. Sparging is started when the vessel is immersed into a preheated oil bath. The resulting inhibition time is 188 minutes.

In Examples 4–5, no inhibitor is added to the system whether done under nitrogen or under air. The polymerization onset occurs after only 6 minutes in each instance, which is the time period required to heat the reaction mass from room temperature to 120° C.

The results of these experiments are shown in the table below.

| Example | 1-Oxyl Inhibitor (ppm) | Initial Atmosphere | Sparge Rate mL/min | Inhibition Time (min) |
| --- | --- | --- | --- | --- |
| 1 | 500 | nitrogen | none | 50 |
| 2 | 500 | air(static) | none | 147 |
| 3 | 500 | nitrogen | 0.4 | 188 |
| 4* | none | nitrogen | none | 6 |
| 5* | none | air(static) | none | 6 |

*The six minute delay in the start of polymerization largely reflects the time needed to heat the samples from 25° C. to 120° C. These examples demonstrate that with the vinyl aromatic monomers such as styrene, unlike other unsaturated monomers such as acrylic acid, oxygen alone is not an effective polymerization inhibitor.

EXAMPLES 6–8

The addition of air is also used as a short-stop of polymerization once polymerization has started under anaerobic conditions. Thus, the experiment of Example 1 is repeated under strictly anaerobic conditions. At the end of the normal inhibition time of ca. 50 minutes, polymerization starts and is allowed to proceed for ten minutes. This results in a styrene polymer content of 1%. At that point a single addition of 50 mL of air is injected into the solution at a rate of 6 mL/min. This air quantity contains 10.5 ml (0.43 mmoles) or 14 mg of oxygen which mounts to 140 ppm of oxygen relative to styrene. As a result the polymerization ceases instantaneously and onset of further polymerization is delayed by an additional 65 minutes.

Even longer delay times are achieved by the injection of higher air volumes. Thus, 500 ml of air, delivered over 10 minutes at 50 mL/minute produced 98 additional minutes of inhibition time. Continuous air sparging at 50 mL/min resulted in 135 minutes additional delay before polymerization onset. Controlled sparging with air thus represents a means not only to boost the efficiency of nitroxyl inhibitors, but also to quench incipient polymerization instantaneously once it starts.

These results are summarized in the table below.

| Example | 1-Oxyl Inhibitor (ppm) | Initial Atmosphere | Volume Air Added mL | Inhibition Time (min) |
| --- | --- | --- | --- | --- |
| 1 | 500 | nitrogen | none | 50 |
| 6 | 500 | nitrogen | 50 | 50 + 65 |
| 7 | 500 | nitrogen | 500 | 50 + 98 |
| 8* | 500 | nitrogen | 7000 | 50 + 135 |

EXAMPLE 9

Following the procedure of Example 1 under strictly anaerobic conditions, 541 ppm of 1-oxyl-2,2,6,6-tetramethylpiperidin-4-yl benzoate in styrene is heated at 120° C. and produces the same inhibition time of 50 minutes as the difunctional inhibitor of Example 1. The molar nitroxyl concentration of this monofunctional derivative is the same as the molar nitroxyl group concentration of the difunctional derivative of Example 1.

EXAMPLE 10

Under an air atmosphere and additional continuous air sparging at a rate of 2 mL/min, 100 g of styrene is heated at 120° C. in presence of 500 ppm of 1-oxyl-2,2,6,6-tetramethylpiperidin-4-yl benzoate. Polymerization onset is only seen after 190 minutes of total inhibition time. In this case the air addition results in a fourfold increase in inhibitor effectiveness compared to the same inhibitor used in Example 9, but without the addition of air to the system.

EXAMPLES 11–16

To ascertain the performance of a variety of other hindered amine nitroxyl derivatives under aerobic and anaerobic conditions, samples of styrene solutions containing 500 ppm of various nitroxyl inhibitors are heated in sealed vials in a forced draft oven at 120° C. vials under air as well as under nitrogen atmospheres. The onset of polymerization is again determined from sudden shifts of refractive index. Inhibition times under air and nitrogen are tabulated below.

| | Inhibition Time (minutes) | |
| --- | --- | --- |
| Example * | Nitrogen | Air |
| 11 | 98 | 210 |
| 12 | 70 | 146 |
| 13 | 72 | 147 |
| 14 | 75 | 134 |
| 15 | 73 | 142 |
| 16 | 79 | 140 |

*
11 - 1-oxyl-2,2,6,6-tetramethylpiperidine
12 - bis(1-oxyl-2,2,6,6-tetramethylpiperidin-4-yl) n-butylmalonate
13 - bis(1-oxyl-2,2,6,6-tetramethylpiperidin-4-yl) succinate
14 - bis(1-oxyl-2,2,6,6-tetramethylpiperidin-4-yl) hexahydroterephthalate
15 - 1-oxyl-2,2,6,6-tetramethylpiperidin-4-yl 4-tert-butylbenzoate
16 - 1-oxyl-2,2,6,6-tetramethylpiperidin-4-yl propionate These results clearly show that the instant nitroxyl compounds generally are very effective inhibitors for vinyl aromatic monomers such as styrene, and that their effectiveness as inhibitors can be greatly enhanced by the concomitant presence of oxygen as seen by the prolonged inhibition times when air is present.

What is claimed is:

1. A composition which comprises
   (a) a vinyl aromatic compound, and
   (b) an effective inhibiting mount, sufficient to prevent premature polymerization during distillation or purification of said vinyl aromatic compound, of a stable hindered nitroxyl compound used together with an effective amount of oxygen or air to enhance the inhibiting activity of the nitroxyl compound.

2. A composition according to claim 1 wherein the effective amount of nitroxyl compound is from 1 to 2000 ppm, based on the weight of component (a).

3. A composition according to claim 2 wherein the amount of nitroxyl compound is from 5 to 1000 ppm, based on the weight of component (a).

4. A composition according to claim 1 wherein the effective amount of oxygen or air is 10 ppm to about 1000 ppm, based on the weight of component (a).

5. A composition according to claim 1 wherein the vinyl aromatic compound of component (a) is selected from the group consisting of styrene, α-methylstyrene, vinyltoluene, divinylbenzene, styrenesulfonic acid and structural isomers, derivatives of said compounds and mixtures thereof.

6. A composition according to claim 5 wherein the vinyl aromatic compound is styrene, α-methylstyrene, vinyltoluene or divinylbenzene.

7. A composition according to claim 6 wherein the vinyl aromatic compound is styrene.

8. A composition according to claim 1 wherein the stable hindered nitroxyl compound of component (b) is selected from the group consisting of di-tert-butyl nitroxyl, 1-oxyl-2,2,6,6-tetramethylpiperidine, 1-oxyl-2,2,6,6-tetramethylpiperidin-4-ol, 1-oxyl-2,2,6,6-tetramethylpiperidin-4-one, 1-oxyl-2,2,6,6-tetramethylpiperidin-4-yl acetate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl 4-tert-butylbenzoate, bis(1-oxyl-2,2,6,6-tetramethylpiperidin-4-yl)succinate, bis(1-oxyl-2,2,6,6-tetramethylpiperidin-4-yl)adipate, bis(1-oxyl-2,2,6,6-tetramethylpiperidin-4-yl)sebacate, bis(1-oxyl-2,2,6,6-tetramethylpiperidin-4-yl)n-butylmalonate, bis(1-oxyl-2,2,6,6-tetramethylpiperidin-4-yl)phthalate, bis(1-oxyl-2,2,6,6-tetramethylpiperidin-4-yl)isophthalate, bis(1-oxyl-2,2,6,6-tetramethylpiperidin-4-yl)terephthalate, bis(1-oxyl-2,2,6,6-tetramethylpiperidin-4-yl)hexahydroterephthalate, N,N'-bis(1-oxyl-2,2,6,6-tetramethylpiperidin-4-yl)adipamide, N-(1-oxyl-2,2,6,6-tetramethylpiperidin-4-yl)-caprolactam, N-(1-oxyl-2,2,6,6-tetramethylpiperidin-4-yl)-dodecylsuccinimide, 2,4,6-tris(1-oxyl-2,2,6,6-tetramethylpiperidin-4-yl isocyanurate, 2,4,6-tris-[N-butyl-N-(1-oxyl-2,2,6,6-tetramethylpiperidin-4-yl]-s-triazine, and 4,4'-ethylenebis(1-oxyl-2,2,6,6-tetramethylpiperazin-3-one).

9. A composition according to claim 8 wherein the compound of component (b) is bis(1-oxyl-2,2,6,6-tetramethylpiperidin-4-yl)sebacate, 1-oxyl-2,2,6,6-tetramethylpiperidine, bis(1-oxyl-2,2,6,6-tetramethylpiperidin-4-yl)n-butylmalonate, bis(1-oxyl-2,2,6,6-tetramethylpiperidin-4-yl)succinate, bis(1-oxyl-2,2,6,6-tetramethylpiperidin-4-yl)hexahydroterephthalate, 1-oxyl-2,2,6,6-tetramethylpiperidin-4-yl 4-tert-butylbenzoate, 1-oxyl-2,2,6,6-tetramethylpiperidin-4-yl propionate, or 1-oxyl-2,2,6,6-tetramethylpiperidin-4-yl benzoate.

10. A composition according to claim 1 which additionally contains a solvent or dissolved polymer.

11. A composition according to claim 10 wherein the solvent is ethylbenzene or the dissolved polymer is a saturated or unsaturated polyester.

* * * * *

(12) REEXAMINATION CERTIFICATE (4329th)
United States Patent
Winter et al.

(10) Number: US 5,545,782 C1
(45) Certificate Issued: May 1, 2001

(54) METHOD FOR INHIBITING PREMATURE POLYMERIZATION OF VINYL AROMATIC MONOMERS

(75) Inventors: Roland A. E. Winter, Armonk; Volker H. von Ahn, Mahopac, both of NY (US)

(73) Assignee: Ciba-Geigy Corporation, Tarrytown, NY (US)

Reexamination Request:
No. 90/004,594, Apr. 4, 1997

Reexamination Certificate for:
Patent No.: 5,545,782
Issued: Aug. 13, 1996
Appl. No.: 08/443,051
Filed: May 17, 1995

Related U.S. Application Data

(60) Division of application No. 08/383,279, filed on Feb. 3, 1995, which is a continuation-in-part of application No. 08/345,097, filed on Nov. 28, 1994, now abandoned.

(51) Int. Cl.[7] .................................................. C07C 7/20
(52) U.S. Cl. ............................... 585/5; 585/4; 585/435; 585/832
(58) Field of Search ........................... 585/3, 4, 5, 832, 585/422, 435

(56) References Cited

U.S. PATENT DOCUMENTS

| | | | |
|---|---|---|---|
| 3,163,677 | 12/1964 | Hoffman et al. | 260/583 |
| 3,334,103 | 8/1967 | Feldman et al. | 260/290 |
| 3,502,692 | 3/1970 | Feldman et al. | 260/326.3 |
| 4,774,374 * | 9/1988 | Abruscato et al. | 585/24 |
| 5,254,760 | 10/1993 | Winter et al. | 585/5 |

OTHER PUBLICATIONS

Muchnik et al., Gas–Chromatographic Investigation of the Solubility of Air in Organic Liquids, Zhurnal Prikladnoi Khimmi, Vol. 8, No. 6, pp. 1322–1325 (Jun. 1975).

Hawley's Condensed Chemical Dictionary, 11th ed. Van Nostrand Publishing Company, Inc. p. 479 (1987).

* cited by examiner

*Primary Examiner*—Bekir L. Yildirim

(57) ABSTRACT

Nitroxyl inhibitors in combination with some oxygen reduce the premature polymerization of vinyl aromatic monomers during the manufacturing processes for such monomers. Even small quantities of air used in combination with the nitroxyl inhibitors result in vastly prolonged inhibition times for said monomers.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–11 are cancelled.

* * * * *